United States Patent
Meitz et al.

(10) Patent No.: US 11,808,708 B2
(45) Date of Patent: Nov. 7, 2023

(54) METHOD FOR MAINTAINING THE HEALTH OF A DIABETIC PATIENT BY PREVENTING THE OCCURRENCE OF DIABETIC KETOACIDOSIS

(71) Applicant: F.A.T. Stats LLC, East Norriton, PA (US)

(72) Inventors: Tom Meitz, Audubon, PA (US); Frank Puglisi, East Norriton, PA (US)

(73) Assignee: F.A.T. STATS LLC, East Norriton, PA (US)

( * ) Notice: Subject to any disclaimer, the term of this patent is extended or adjusted under 35 U.S.C. 154(b) by 157 days.

(21) Appl. No.: 17/395,916

(22) Filed: Aug. 6, 2021

(65) Prior Publication Data
US 2022/0050057 A1    Feb. 17, 2022

Related U.S. Application Data

(60) Provisional application No. 63/064,716, filed on Aug. 12, 2020.

(51) Int. Cl.
*G01N 21/78* (2006.01)
*A61K 31/7034* (2006.01)

(52) U.S. Cl.
CPC ......... *G01N 21/78* (2013.01); *A61K 31/7034* (2013.01)

(58) Field of Classification Search
None
See application file for complete search history.

(56) References Cited

U.S. PATENT DOCUMENTS

| | | |
|---|---|---|
| 4,147,514 A | 4/1979 | Magers et al. |
| 4,837,331 A | 6/1989 | Yamanishi et al. |
| 5,902,731 A | 5/1999 | Ouyang et al. |
| 6,586,199 B2 | 7/2003 | Ouyang et al. |
| 6,703,216 B2 | 3/2004 | Parsons et al. |
| 6,762,035 B1 * | 7/2004 | Gupta .................. G01N 33/523 435/26 |
| 9,416,397 B2 | 8/2016 | Wilsey |
| 2004/0043376 A1 | 3/2004 | Gupta |
| 2007/0202090 A1 | 8/2007 | Prosek et al. |
| 2009/0208989 A1 | 8/2009 | Petrich et al. |
| 2021/0147900 A1 | 5/2021 | Meitz et al. |

FOREIGN PATENT DOCUMENTS

| | | |
|---|---|---|
| CN | 102435749 A | 5/2012 |
| EP | 2636750 A1 | 9/2013 |
| WO | 2005/111224 A2 | 11/2005 |

OTHER PUBLICATIONS

Kerl, Marie E. "Diabetic ketoacidosis: pathophysiology and clinical and laboratory presentation." Compendium 23.3 (2001): 220-228.*
Cafalu et al. Diabetologia (2015), vol. 58, pp. 1183-1187.*
Giordani et al, "Evidence for two different electron transfer pathways in the same enzyme, nitrate reductase A from *Escherichia coli*" Eur. J. Biochem. 271, 2400-2407 (2004).
Sampedro et al, "Trehalose-enzyme interactions result in structure stabilization and activity inhibition. The role of viscosity" Molecular and Cellular Biochemistry, 256/257 319-327 (2004).
Wang et al. "An optical material for the detection of ß-hydroxybutyrate based on a terbium complex", Optical Materials, vol. 36, p. 809-812 (2014).

* cited by examiner

*Primary Examiner* — Patrick T Lewis
(74) *Attorney, Agent, or Firm* — Armstrong Teasdale LLP

(57) ABSTRACT

A method for maintaining the health of a diabetic patient by preventing onset of diabetic ketoacidosis in said patient, the method comprising: prescribing an SGLT2 inhibitor for administration to a patient in need thereof; providing at least one test strip for identifying the presence of β-hydroxybutyrate in the patient's urine; and upon indication of the presence of β-hydroxybutyrate in the patient's urine, discontinuing the administration of the SGLT2 inhibitor. Also disclosed is a kit useful in the monitoring of risk of onset of diabetic ketoacidosis in patients taking an SGLT2 inhibitor, the kit comprising: the SGLT2 inhibitor and at least one test strip to identify the presence of β-hydroxybutyrate in the patient's urine, wherein the at least one test strip undergoes a change in color upon detection of β-hydroxybutyrate in the patient's urine.

18 Claims, No Drawings

METHOD FOR MAINTAINING THE HEALTH OF A DIABETIC PATIENT BY PREVENTING THE OCCURRENCE OF DIABETIC KETOACIDOSIS

CROSS-REFERENCE TO RELATED APPLICATIONS

This application claims the benefit of priority under 35 U.S.C. § 119(e) to earlier filed U.S. Provisional Patent Application No. 63/064,716 filed Aug. 12, 2020, the entire disclosure of which is incorporated by reference herein.

BACKGROUND OF THE INVENTION

The present invention relates to the prevention of diabetic ketoacidosis in a diabetic patient taking sodium-glucose cotransporter 2 inhibitors. In particular, the present invention relates to the prevention of diabetic ketoacidosis in a diabetic patient taking sodium-glucose cotransporter 2 inhibitors by providing a urine test for β-hydroxybutyrate to be self-administered by the patient in conjunction with taking sodium-glucose cotransporter 2 inhibitors.

Sodium-glucose cotransporter 2 (SGLT2) inhibitors are a relatively new class of anti-diabetic medications that act by limiting glucose reabsorption in the kidney at a lower threshold through inhibition of SGLT2 in the distal nephron. This causes renal glucosuria, resulting in lower blood glucose. SGLT2s can be used in both Type 1 and Type 2 diabetic patients.

Unfortunately, this class of anti-diabetic medications comes with a potential side effect of Diabetic Ketoacidosis (DKA). DKA incidence in patients receiving an SGLT2 inhibitor has been reported as high as 1/1000 patients.

Diabetic ketoacidosis is a serious complication of diabetes that occurs when the body produces high levels of blood acids called ketones (specifically β-hydroxybutyrate (BHB)). The condition develops when a body can't produce enough insulin. Insulin normally plays a key role in helping sugar (glucose)—a major source of energy for your muscles and other tissues—enter cells. Without enough insulin, a person's body begins to break down fat as fuel. This process produces a buildup of acids in the bloodstream called ketones (specifically Beta-hydroxybutyrate (BHB), eventually leading to diabetic ketoacidosis and possible death.

For example, in May 2015, the U.S. Food and Drug Administration (FDA) issued a Drug Safety Communication warning that treatment with SGLT2 inhibitors may increase the risk of ketoacidosis. From March 2013 to June 2014, 20 cases of acidosis reported as diabetic ketoacidosis (DKA), ketoacidosis, or ketosis in patients treated with SGLT2 inhibitors were reported to the FDA Adverse Events Reporting System (FAERS); all of these patients required emergency treatment or hospitalization. These FAERS cases were atypical for DKA because most of the patients had type 2 diabetes and their blood sugar levels were only slightly increased compared to the high blood sugar levels seen in typical cases of DKA.

Symptoms of DKA include nausea, vomiting, excessive thirst and urine production, abdominal pain, labored breathing, fatigue, and coma, amongst others. Given the seriousness of DKA, it is desirable to administer treatment to reduce ketone levels before the full onset of a DKA episode. Further, since symptoms related to a DKA episode may not present until the DKA episode has onset or ketone levels are otherwise undesirably high, it is generally preferred for ketone reducing treatment not to begin as a response to these symptoms.

SGLT2 inhibitors can induce "normal" DKA where elevated glucose levels or Euglycemic Diabetic Ketoacidosis (EuDKA) is observed. With EuDKA, the patient will show normal or only slightly elevated blood glucose levels. The only two monitoring tools to assess DKA currently available, for patient at home use, are urinary acetoacetate strips or capillary finger-prick BHB strips which also require a meter. Acetoacetate (AcAc) is the first ketone made in the liver as DKA begins. However, AcAc cannot provide energy to human cells and is quickly converted into BHB. Using urine AcAc strips to monitor for DKA is not only inaccurate, it is potentially dangerous because the results could produce either a false positive or false negative of the patients true DKA status. Using capillary finger-prick BHB is a good clinical option in early monitoring of DKA, however, patients simply do not use this method as both cost and the invasive nature are deterrents.

Accordingly, there is a need in the art for a simpler test that can be self-performed by a patient taking an SGLT2 inhibitor for diabetes management that can accurately signal the increased risk or onset of DKA.

BRIEF SUMMARY OF THE INVENTION

This need has been satisfied by the present invention. Disclosed herein is a method for maintaining the health of a diabetic patient by preventing onset of diabetic ketoacidosis in said patient, the method comprising: prescribing a therapeutically effective amount of an SGLT2 inhibitor for administration to a patient in need thereof; providing at least one test strip for identifying the presence of BHB in the patient's urine; and upon indication of the presence of BHB in the patient's urine, discontinuing the administration of the SGLT2 inhibitor.

In another aspect, disclosed herein is a noninvasive method of monitoring for early stages of diabetic ketoacidosis in a patient wherein the patient is taking an SGLT2 inhibitor, the method comprising: providing at least one test strip for identifying the presence of BHB in the patient's urine; and upon indication of the presence of BHB in the patient's urine, discontinuing the SGLT2 inhibitor.

In another aspect, disclosed herein is a kit useful in the monitoring of risk of onset of diabetic ketoacidosis in patients taking an SGLT2 inhibitor, the kit comprising: the SGLT2 inhibitor and at least one test strip to identify the presence of BHB in the patient's urine, wherein the at least one test strip undergoes a change in color upon detection of BHB in the patient's urine.

The embodiments of the invention can be used alone or in combinations with each other.

DETAILED DESCRIPTION OF THE INVENTION

The ensuing detailed description provides preferred exemplary embodiments only, and is not intended to limit the scope, applicability, or configuration of the invention. Rather, the ensuing detailed description of the preferred exemplary embodiments will provide those skilled in the art with an enabling description for implementing the preferred exemplary embodiments of the invention. Various changes may be made in the function and arrangement of elements without departing from the spirit and scope of the invention, as set forth in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. The use of the term "comprising" in the specification and the claims includes the narrower language of "consisting essentially of" and "consisting of."

As used herein, "about" is intended to correspond to ±5% of the stated value.

As used herein, a "subject" refers to an animal, preferably a mammal, such as, for example, a human or non-human primate. In some aspects, the subject is a human and may be referred to as a "patient." A subject may be one who has been previously diagnosed or identified as having prediabetes, type 1 or type 2 diabetes, and optionally has already undergone or is undergoing a therapeutic intervention for prediabetes, type 1 or type 2 diabetes. Alternatively, a subject can also be one who has not been previously diagnosed as having prediabetes, type 1 or type 2 diabetes. For example, a subject can be one who exhibits one or more risk factors for prediabetes, type 1 or type 2 diabetes. Alternatively, a subject may be one who does not exhibit a risk factor for prediabetes, type 1 or type 2 diabetes or who is asymptomatic for prediabetes, type 1 or type 2 diabetes.

As used herein, the phrase "in need thereof" means that the "individual," "subject," or "patient" has been identified as having a need for the particular method, prevention, or treatment. In some embodiments, the identification can be by any means of diagnosis. In any of the methods, preventions, and treatments described herein, the "individual," "subject," or "patient" can be in need thereof. In some embodiments, the "individual," "subject," or "patient" is in an environment or will be traveling to an environment or has traveled to an environment in which a particular disease, disorder, or condition is prevalent.

As used herein, the terms "prevention" or "preventing" mean a reduction of the risk of acquiring a particular disease, condition, or disorder.

As used herein, the phrase "therapeutically effective amount" means the amount of active compound or pharmaceutical agent that elicits the biological or medicinal response that is being sought in a tissue, system, animal, individual or human by a researcher, veterinarian, medical doctor, or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be based on, for example, the age, health, size, and sex of the subject. Optimal amounts can also be determined based on monitoring of the subject's response to treatment. mean a reduction of the risk of acquiring a particular disease, condition, or disorder.

As used herein, the terms "treat," "treated," or "treating" mean both therapeutic treatment and prophylactic or preventative measures wherein the object is to prevent or slow down (lessen) an undesired physiological condition, disorder or disease, or obtain beneficial or desired clinical results. For purposes herein, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment includes eliciting a clinically significant response, optionally without excessive levels of side effects. Treatment also includes prolonging survival as compared to expected survival if not receiving treatment.

At least in some approaches, measurements of one or more biomarkers as described herein may lead to a healthcare provider or practitioner to effectuate a therapy with respect to the subject. The terms "therapy" or "treatment" may be used interchangeably and include, for example, initiating therapy, continuing therapy, modifying therapy, or ending therapy. A therapy may also include any prophylactic measures that may be taken to prevent prediabetes or type 2 diabetes.

The diagnosis provided herein may be used to inform the appropriate treatment for prediabetes, type 1 or type 2 diabetes. At least in some approaches, type 2 diabetes may be managed by increasing exercise and making dietary changes. If blood sugar levels are not adequately lowered by these measures alone, type 2 diabetes is often treated with medication, such as those which (1) stimulate the pancreas to produce and release more insulin; (2) inhibit the production and release of glucose from the liver; (3) block the action of stomach enzymes that break down carbohydrates; and/or (4) improve the sensitivity of cells to insulin. Exemplary medications include but are not limited to metformin, sulfonylureas, meglitinides, thiazolidinediones, DPP-4 inhibitors, GLP-1 receptor agonists, and SGLT2 inhibitors. Insulin therapy may also be used to treat type 2 diabetes.

The present disclosure provides a method and kit for maintaining the health of a diabetic patient taking an SGLT2 inhibitor by preventing onset of diabetic ketoacidosis in the patient. Specifically, disclosed herein is a method for maintaining the health of a diabetic patient by preventing onset of diabetic ketoacidosis in said patient, the method comprising: prescribing an SGLT2 inhibitor for administration to a patient in need thereof; providing at least one test strip for identifying the presence of BHB in the patient's urine; and upon indication of the presence of BHB in the patient's urine, discontinuing the administration of the SGLT2 inhibitor. Also disclosed herein is a kit useful in the monitoring of risk of onset of diabetic ketoacidosis in patients taking an SGLT2 inhibitor, the kit comprising: the SGLT2 inhibitor and at least one test strip to identify the presence of BHB in the patient's urine, wherein the at least one test strip undergoes a change in color upon detection of BHB in the patient's urine.

The method disclosed herein comprises the step of prescribing a therapeutically effective amount of an SGLT2 inhibitor for administration to a patient in need thereof. SGLT2 inhibitors are typically prescribed to patients suffering from type 1 or type 2 diabetes. Type 2 diabetes, for example, is a progressive disease typically requiring multiple medications in order to control blood glucose levels. Sodium-glucose cotransporter-2 (SGLT2) inhibitors are a class of anti-hyperglycemic agents that function through a novel mechanism of reducing renal tubular glucose reabsorption, producing a reduction in blood glucose without stimulating insulin release.

SGLT2 proteins are expressed in the proximal convoluted tubule of the kidneys. These transporters are an ideal target for the treatment of diabetes because they are responsible for roughly 90% of filtered glucose reabsorption. The normal renal threshold for reabsorption of glucose corresponds to a serum glucose concentration of 180 mg/dL. In patients with, for example, type 2 diabetes, this threshold can increase and the expression of the SGLT2 can be upregulated causing a maladaptive response that worsens hyperglycemia. Selective inhibition of SGLT2 inhibitors can reduce this threshold to as low as 40 to 120 mg/dL.

Exemplary SGLT2 inhibitors that have been approved by the U.S. Food and Drug Administration (FDA) include canagliflozin, dapagliflozin, and empagliflozin.

In diabetic ketoacidosis (DKA), absolute insulin deficiency leads to reduced glucose utilization and enhanced lipolysis; increased free fatty acids (FFAs) in the liver coupled with high glucagon levels promote FFA oxidation and production of ketone bodies. DKA presents with hyperglycemia (glucose >250 mg/dL), glycosuria, and hyperketonemia. Euglycemic DKA (euDKA) involves a different mechanism. Full-dose SGLT2 inhibition induces a rapid increase in urinary glucose excretion, ranging 50-100 g/day. Because of the decline in glucose by 20-25 mg/dL, plasma insulin levels also decrease (by ~10 pmol/L fasting and ~60 pmol/L postmeal) with a compensatory increase in glucagon levels. This shift in hormones causes a released inhibition of gluconeogenesis in the liver as well as augmented endogenous glucose production both in the fasting and fed states. Most importantly, renal glucose clearance (i.e., the ratio of glycosuria to prevailing glycemia) is twice as much with euDKA compared to DKA. Thus, in SGLT2-treated type 2 diabetes patients with euDKA, the lower insulin-to-glucagon ratio stimulates lipolysis augmenting FFA delivery to the liver and resulting in mild stimulation of ketogenesis. If insulin deficiency is more profound, as can happen in type 1 diabetes patients, or if carbohydrate availability is drastically restricted, the mild ketosis would evolve toward ketoacidosis. euDKA is pathophysiologically similar to DKA except for the circumstance of SGLT2-induced glycosuria that "artificially" lowers plasma glucose levels and predisposes to increased ketogenesis. These lower glucose levels make identifying euDKA more difficult and may lead to delayed treatment.

The step of prescribing an SGLT2 inhibitor for administration to a patient in need thereof according to the present invention is typically performed by a physician who is licensed to prescribe medications.

The method of the present invention also includes the step of providing at least one test strip for identifying the presence of BHB in the patient's urine. Because the method of the present invention tests for BHB in urine as opposed to blood, the test for identifying the presence of BHB in the patient's urine is noninvasive. In some embodiments, the patient's urine is tested at least once a day. In other embodiments, the patient's urine is tested at least twice a day. In other embodiments, the patient's urine is tested at least three times a day.

Test strips for use in accordance with the present invention comprise a composition for detecting BHB on a carrier. In preferred embodiments, the test strip is designed so that it may be conveniently dipped into or otherwise exposed to urine that potentially may comprise BHB. If the composition for detecting BHB on the carrier undergoes a change in an optical property, for example changes from a light color to a dark color, then a user of the test strip would know that the biological sample contains BHB.

The specific composition is not particularly critical to the practice of the method of the present invention but only that the composition is capable of identifying the presence of BHB in a patient's urine sample. Such compositions are disclosed in, for example, U.S. Provisional Patent Application No. 62/936,946, filed on Nov. 18, 2019, and U.S. Pat. No. 6,762,035, the disclosures of which are incorporated herein by reference in their entireties.

Preferably, the composition undergoes a change in its optical property or properties upon exposure to BHB. The optical property may be observed as a visual color change, e.g., from a light color to a darker color, or from a nearly white color to a purple color. The optical property may also be measured as $\Delta E$, by the use of a color meter, also referred to as a spectrophotometer.

In other embodiments, the composition can emit different shades of colors corresponding to different levels of BHB detected.

An optical property as referred to herein refers to an optical property of the composition for detecting BHB. The optical property of the composition for detecting BHB may be due to an optical property of an indicator reagent that is often part of the composition which can be optically detected. Non-limiting examples of such optical properties are light absorption or emission, re-emission, refraction or polarization and properties associated therewith. It will be understood that a change of at least one optical property as used herein, may encompass the detection of the presence of a property which was not detectable before, the detection of the absence of a property which has been detected before and the detection of quantitative changes of a property, i.e., the detection of the change of the signal strength which correlates to the extent of the change of the at least optical property. Optical properties contemplated by the present invention may be color, including color that can be detected visually, or by the use of a color meter that utilizes the CIELAB color space (also referred to as CIE L*a*b), as defined by the International Commission on Illumination. Other non-limiting examples of optical properties may be fluorescence, luminescence, or refractometry, for example, a change in refractive index. The optical properties which may change or may be observed according to the present invention may depend on the type and level of the indicator reagent. A change in color, as for instance, from a yellow or white color to a purple color that can be detected visually is contemplated. A change in $\Delta E$ measured with a color meter is contemplated.

The carrier portion of the test strip may comprise a porous material, such as filter paper, for example, Whatman filter paper #4 or similar. In other embodiments, the carrier portion of the test strip may further comprise an inert water-resistant substrate attached to the porous material. The inert water-resistant substrate may render the carrier easier to handle, for example, if the composition on the carrier is exposed to BHB by being dipped into urine. Non-limiting examples of such inert water-resistant substrates may be plastic sheets such as polyethylene, polypropylene, acrylics, polyesters, polycarbonate, polyvinylchloride, polystyrene.

The method of the present invention also includes the step of, upon indication of the presence of BHB in the patient's urine, discontinuing the administration of the SGLT2 inhibitor. If BHB is detected in an SGLT2 inhibitor patient's urine, then the patient should stop taking the SGLT2 inhibitor and contact his/her healthcare provider or the prescribing physician for further treatment. The patient should be so instructed by the prescribing physician to prevent the onset of diabetic ketoacidosis.

The level of BHB in the patient's urine may range from 0.2 mM to 4.0 mM, or from 0.05 mM to 8.0 mM, or from 0.1 mM to 7 mM, or from 0.25 mM to 6 mM, or from 0.2 mM to 5 mM, or from 0.05 mM to 4.0 mM, or from 2.0 mM to 4 mM, or from 0.5 mM to 5 mM, or from 1 mM to 5 mM, or from 0.3 mM to 4 mM, or from 1.5 mM to 5.5 mM, or from 0.3 mM to 4 mM, or from 1 mM to 6.0 mM, or from 1 mM to 3.0 mM, limits inclusive.

Accordingly, the present invention also provides a non-invasive method of monitoring for early stages of diabetic ketoacidosis in a patient wherein the patient is taking an SGLT2 inhibitor, the method comprising: providing at least one test strip for identifying the presence of BHB in the patient's urine; and upon indication of the presence of BHB in the patient's urine, discontinuing the SGLT2 inhibitor The present invention also provides pharmaceutical packs or kits comprising the prescribed SGLT2 inhibitor and at least one test strip to identify the presence of BHB in the patient's urine, wherein the at least one test strip undergoes a change in color upon detection of BHB in the patient's urine. The number of test strips in the kit may, for example, correspond to the number of tests that are recommended per day per a time period of the prescription such as, for example, one month. Thus, if one test per day is required, the kit can comprise about 30 test strips. If three tests per day are required, the kit can comprise about 90 test strips. Optionally associated with such kits can be a notice in the form prescribed by a governmental agency regulating the manufacture, use or sale of pharmaceuticals or biological products, which notice reflects approval by the agency of manufacture, use or sale for human administration for treating a condition, disease, or disorder described herein.

The invention claimed is:

1. A method of monitoring for the onset of diabetic ketoacidosis in a diabetic patient, the method comprising:
   providing at least one test strip for identifying the presence of β-hydroxybutyrate in the diabetic patient's urine, wherein the diabetic patient is taking an SGLT2 inhibitor;
   continuing the SGLT2 inhibitor as directed when β-hydroxybutyrate is not indicated on the at least one test strip; and
   discontinuing the SGLT2 inhibitor upon indication of the presence of β-hydroxybutyrate in the diabetic patient's urine to prevent the onset of diabetic ketoacidosis.

2. The method of claim 1 wherein the SGLT2 inhibitor is selected from the group consisting of canagliflozin, dapagliflozin, and empagliflozin.

3. The method of claim 1 wherein the test strip changes color upon exposure to urine comprising β-hydroxybutyrate.

4. The method of claim 1 wherein the test strip comprises a carrier and a composition for detecting β-hydroxybutyrate in urine.

5. The method of claim 4 wherein the carrier comprises a porous substrate.

6. The method of claim 1 wherein the diabetic patient is instructed to use the test strip to test for the presence of β-hydroxybutyrate in the diabetic patient's urine at least one time per day.

7. A method of monitoring for the onset of diabetic ketoacidosis in a diabetic patient, the method comprising:
   exposing a test strip to the diabetic patient's urine, wherein the test strip can identify the presence of β-hydroxybutyrate in the diabetic patient's urine, wherein the diabetic patient is taking an SGLT2 inhibitor;
   continuing the SGLT2 inhibitor as directed when β-hydroxybutyrate is not indicated on the at least one test strip; and
   discontinuing the SGLT2 inhibitor upon indication of the presence of β-hydroxybutyrate in the diabetic patient's urine to prevent the onset of diabetic ketoacidosis.

8. The method of claim 7 wherein the SGLT2 inhibitor is selected from the group consisting of canagliflozin, dapagliflozin, and empagliflozin.

9. The method of claim 7 wherein the test strip changes color upon exposure to urine comprising β-hydroxybutyrate.

10. The method of claim 7 wherein the test strip comprises a carrier and a composition for detecting β-hydroxybutyrate in urine.

11. The method of claim 10 wherein the carrier comprises a porous substrate.

12. The method of claim 7 wherein the diabetic patient is directed to use the test strip to test for the presence of β-hydroxybutyrate in the diabetic patient's urine at least one time per day.

13. A method of treating a diabetic patient with an SGLT2 inhibitor to prevent the diabetic patient from suffering from diabetic ketoacidosis, the method comprising the steps of:
   exposing a test strip to the diabetic patient's urine, wherein the test strip can identify the presence of β-hydroxybutyrate in the diabetic patient's urine, wherein the diabetic patient is taking an SGLT2 inhibitor;
   continuing the SGLT2 inhibitor as directed when β-hydroxybutyrate is not indicated on the at least one test strip; and
   discontinuing the SGLT2 inhibitor upon indication of the presence of β-hydroxybutyrate in the diabetic patient's urine to prevent the onset of diabetic ketoacidosis.

14. The method of claim 13 wherein the SGLT2 inhibitor is selected from the group consisting of canagliflozin, dapagliflozin, and empagliflozin.

15. The method of claim 13 wherein the test strip changes color upon exposure to urine comprising β-hydroxybutyrate.

16. The method of claim 13 wherein the test strip comprises a carrier and a composition for detecting β-hydroxybutyrate in urine.

17. The method of claim 16 wherein the carrier comprises a porous substrate.

18. The method of claim 13 wherein the diabetic patient is directed to use the test strip to test for the presence of β-hydroxybutyrate in the diabetic patient's urine at least one time per day.

* * * * *